United States Patent
Harding, Jr.

(10) Patent No.: US 9,144,500 B2
(45) Date of Patent: Sep. 29, 2015

(54) ANKLE REPLACEMENT DEVICES AND METHODS OF MAKING AND USING THE SAME

(71) Applicant: Michael G. Harding, Jr., McDonough, GA (US)

(72) Inventor: Michael G. Harding, Jr., McDonough, GA (US)

(*) Notice: Subject to any disclaimer, the term of this patent is extended or adjusted under 35 U.S.C. 154(b) by 0 days.

(21) Appl. No.: 14/033,109

(22) Filed: Sep. 20, 2013

(65) Prior Publication Data

US 2014/0180427 A1    Jun. 26, 2014

Related U.S. Application Data

(60) Provisional application No. 61/703,282, filed on Sep. 20, 2012.

(51) Int. Cl.
*A61F 2/42* (2006.01)
*A61F 2/30* (2006.01)

(52) U.S. Cl.
CPC ............ *A61F 2/4202* (2013.01); *A61F 2/3094* (2013.01); *A61F 2002/30253* (2013.01); *A61F 2002/30387* (2013.01); *A61F 2002/30578* (2013.01); *A61F 2002/30878* (2013.01); *A61F 2002/30934* (2013.01); *A61F 2002/4205* (2013.01); *A61F 2002/4207* (2013.01)

(58) Field of Classification Search
CPC ........... A61F 2/4202; A61F 2002/4207; A61F 2002/42; A61F 2002/421
USPC ....................................................... 623/21.18
See application file for complete search history.

(56) References Cited

U.S. PATENT DOCUMENTS

| | | |
|---|---|---|
| 3,839,742 A | 10/1974 | Link |
| 3,872,519 A | 3/1975 | Giannestras et al. |
| 3,889,300 A | 6/1975 | Smith |
| 3,975,778 A | 8/1976 | Newton, III |
| 4,069,518 A | 1/1978 | Groth et al. |
| 4,470,158 A | 9/1984 | Pappas et al. |
| 5,177,883 A | 1/1993 | Darby |
| 5,326,365 A | 7/1994 | Alvine |
| 5,658,341 A | 8/1997 | Delfosse |
| 5,824,106 A | 10/1998 | Fournol |
| 6,409,767 B1 | 6/2002 | Perice et al. |
| 6,863,691 B2 | 3/2005 | Short et al. |
| 2003/0204265 A1* | 10/2003 | Short et al. ................. 623/21.18 |
| 2012/0109326 A1* | 5/2012 | Perler ........................ 623/21.18 |

* cited by examiner

*Primary Examiner* — Jason-Dennis Stewart
(74) *Attorney, Agent, or Firm* — Withers & Keys, LLC

(57) ABSTRACT

Ankle replacement devices are disclosed. Methods of making and using ankle replacement devices are also disclosed.

19 Claims, 14 Drawing Sheets

ANKLE REPLACEMENT DEVICES AND METHODS OF MAKING AND USING THE SAME

CROSS-REFERENCE TO RELATED APPLICATIONS

This patent application claims the benefit of priority to (i) U.S. provisional patent application Ser. No. 61/703,282 entitled "ANKLE REPLACEMENT DEVICES AND METHODS OF MAKING AND USING THE SAME" filed on Sep. 20, 2012, the subject matter of which is incorporated herein in its entirety.

FIELD OF THE INVENTION

The present invention relates to ankle replacement devices and methods of making and using ankle replacement devices.

BACKGROUND OF THE INVENTION

Total ankle arthroplasty is a common treatment to replace the damaged talocrural joint due to wear, fatigue, and trauma. This joint structure can be damaged from arthritis, bone fractures, displasia, or other degenerative mechanisms. Many of the FDA-approved devices only feature a saddle-type joint that allows flexion and extension, but limited talocrural stability during inversion and eversion. Further, the structure of ankle replacement devices currently available on the U.S. market also have an ability to dislocate from internal rotations that exist on the tibia and talus during loading. In addition, current total ankle replacements are static in displacement and cannot be adjusted post-operation for limb length discrepancies that are found in the patient.

There exists a need in the art for improved ankle replacement devices that (i) allow flexion and extension, as well as increased stability for inversion and eversion joint movements, (ii) allows for length adjustments to account for limb length discrepancies that are found in many patients, and (iii) provide years of normal patient use.

SUMMARY OF THE INVENTION

The present invention is directed to ankle replacement devices. The ankle replacement devices of the present invention have been designed to (i) provide a reliable total joint replacement for the talocrural joint designed for stability, range of motion, and wear resistance, and (ii) to allow for an optional lengthening mechanism for minimizing length variation of the lower extremities.

In one exemplary embodiment, the device of the present invention comprises an ankle replacement device comprising a first bone-engaging component operatively adapted to engage with a first bone, and comprising a first base member comprising a lower surface, the lower surface having an lower surface profile comprising (i) a lower surface portion surrounded by a lower surface periphery, and (ii) a lower surface depression surrounded by the lower surface portion, the lower surface depression having a dome-shaped (or any shape having a dome-like feature, e.g., an ellipsoid shape) configuration with a depression depth and a depression surface area extending along the lower surface portion; and a second bone-engaging component operatively adapted to engage with a second bone, and comprising an upper surface, the upper surface having an upper surface profile comprising (i) an upper surface portion surrounded by an upper surface periphery, and (ii) an upper surface structure surrounded by the upper surface portion, the upper surface structure having a dome-shaped configuration with a structure height extending above the upper surface portion and a structure surface area extending along the upper surface portion; the first bone-engaging component being engagable with the second bone-engaging component so that (i) at least a portion of the upper surface structure is positionable within the lower surface depression, and (ii) when the portion of the upper surface structure is positioned within the lower surface depression, the upper surface portion is movable relative to the lower surface portion.

The present invention is further directed to methods of making any of the herein-disclosed ankle replacement devices. In one exemplary embodiment, the method of making an device of the present invention comprises (I) forming a first bone-engaging component operatively adapted to engage with a first bone, the first bone-engaging component comprising a first base member comprising a lower surface, the lower surface having an lower surface profile comprising (i) a lower surface portion surrounded by a lower surface periphery, and (ii) a lower surface depression surrounded by the lower surface portion, the lower surface depression having a dome-shaped configuration with a depression depth and a depression surface area extending along the lower surface portion; and (II) forming a second bone-engaging component operatively adapted to engage with a second bone, the second bone-engaging component comprising an upper surface, the upper surface having an upper surface profile comprising (i) an upper surface portion surrounded by an upper surface periphery, and (ii) an upper surface structure surrounded by the upper surface portion, the upper surface structure having a dome-shaped configuration with a structure height extending above the upper surface periphery and a structure surface area extending along the upper surface portion; wherein the first bone-engaging component is engagable with the second bone-engaging component so that (i) at least a portion of the upper surface structure is positionable within the lower surface depression, and (ii) when the portion of the upper surface structure is positioned within the lower surface depression, the upper surface portion is movable relative to the lower surface portion.

The present invention is even further directed to methods of using any of the herein-disclosed ankle replacement devices. In one exemplary embodiment, the method of using an ankle replacement device of the present invention comprises implanting a first bone-engaging component into a patient, the first bone-engaging component being operatively adapted to engage with a first bone, and comprising a first base member comprising a lower surface, the lower surface having an lower surface profile comprising (i) a lower surface portion surrounded by a lower surface periphery, and (ii) a lower surface depression surrounded by the lower surface portion, the lower surface depression having a dome-shaped configuration with a depression depth and a depression surface area extending along the lower surface portion; and (II) implanting a second bone-engaging component into a patient, the second bone-engaging component being operatively adapted to engage with a second bone, and comprising an upper surface, the upper surface having an upper surface profile comprising (i) an upper surface portion surrounded by an upper surface periphery, and (ii) an upper surface structure surrounded by the upper surface portion, the upper surface structure having a dome-shaped configuration with a structure height extending above the upper surface periphery and a structure surface area extending along the upper surface portion; wherein the first bone-engaging component is engagable with the second bone-engaging component so that (i) at least a portion of the upper surface structure is positionable within the lower surface depression, and (ii) when the portion of the upper surface structure is positioned within the lower surface depression, the upper surface portion is movable relative to the lower surface portion.

The methods of using any of the herein-disclosed ankle replacement devices of the present invention may further comprise one or more additional steps including, but not limited to, attaching the first bone-engaging component to a first bone; and attaching the second bone-engaging component to a second bone. In some desired embodiments, the device of the present invention is used to replace an ankle of the patient.

These and other features and advantages of the present invention will become apparent after a review of the following detailed description of the disclosed embodiments and the appended claims.

BRIEF DESCRIPTION OF THE FIGURES

The present invention is further described with reference to the appended figures showing exemplary embodiments of the present invention, wherein.

DETAILED DESCRIPTION OF THE INVENTION

The present invention is directed to ankle replacement devices and methods of making and using ankle replacement devices. In particular, the present invention is directed to ankle replacement devices as shown in the figures, as described in the various embodiments shown and described herein, and as recited in the claims below. An exemplary device 10 of the present invention is shown, for example, in FIGS. 1-8D. Another exemplary device 10 of the present invention is shown, for example, in FIGS. 9-22B.

The ankle replacement devices of the present invention provide a patient with a stable ankle replacement and gives the physician an opportunity for limb length correction based on any pre-existing limb length discrepancy measurements.

Historically, total ankle replacements have exhibited a probability of undergoing dislocation and component loosening during certain ankle movements. If internal rotation exists in the talus or tibia and the external force is great enough, the two components can separate or loosen due to joint instability. The coupling interface at the tibial and talar junction provides a semi-constrained encapsulation that uses a bearing surface on two depressed tracks to maintain joint integrity and physiological function.

Current total ankle replacements are static in displacement and do not account for limb length correction due to variations that can occur prior or after the arthroplasty procedure has taken place. When the talar and tibial components are inserted, bone cement and/or biocompatible screws are used to fixate the components to bones. The disclosed device may be fixated to the tibia and talus using porous ceramic bone cement and/or bone screws. This type of bone cement provides a pathway for osteoclasts and osteoblasts to reconstruct scaffolding of the bone, which forms a biomaterial-bone integrated interface. This interface allows the material to become part of the bone and ensures fixation stability.

To the implementing physicians installing the disclosed device, the disclosed device is similar to other available prostheses in size. In an operation scenario, the supporting physicians and/or nurses would measure limb length in pre-operation procedures to plan for the tibial and talar shearing. To account for the shearing length, the disclosed device would be set to an initial height and the appropriate spacer inserted (manufactured) prior to surgery so that the doctor will be able to insert the disclosed device as a two-component device. Aside from proper training on how to sufficiently raise or lower the disclosed device to account for limb length correction, the implantation procedure will be similar to those already in place.

The disclosed device gives physicians a way of accounting for limb length discrepancies in patients. The displacement mechanism and locking mechanism enable the disclosed device to provide structural stability, as well as, account for post-operation discrepancies that can occur in patients.

Figure 1:
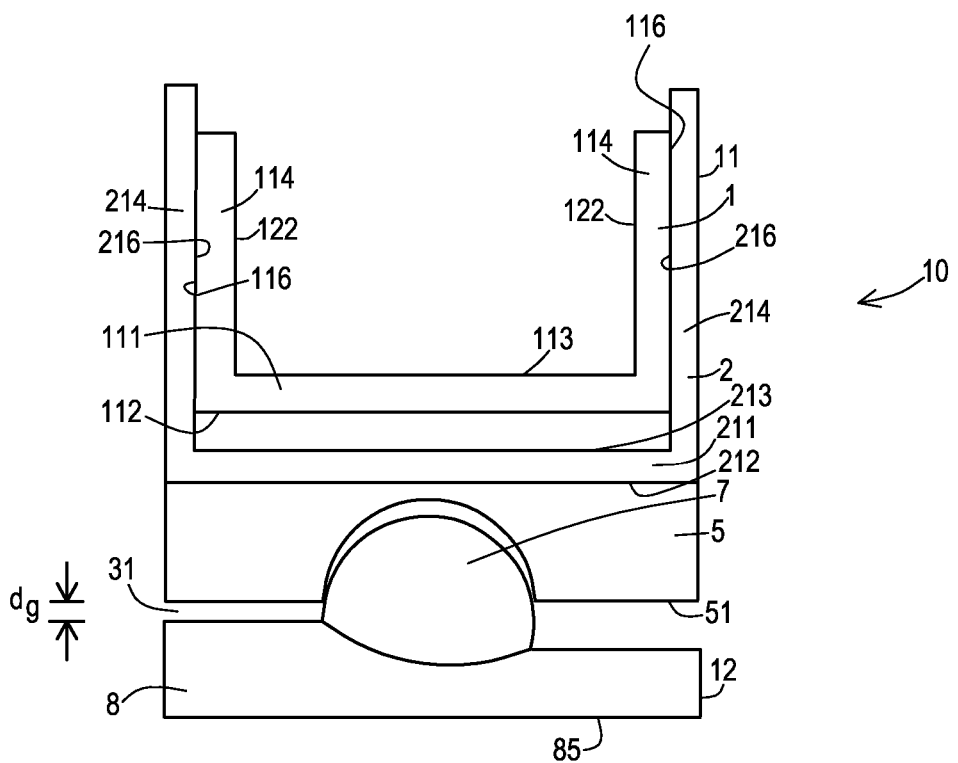
FIG. 1 depicts a side cross-sectional view of an exemplary ankle replacement device of the present invention.
Figure 2:
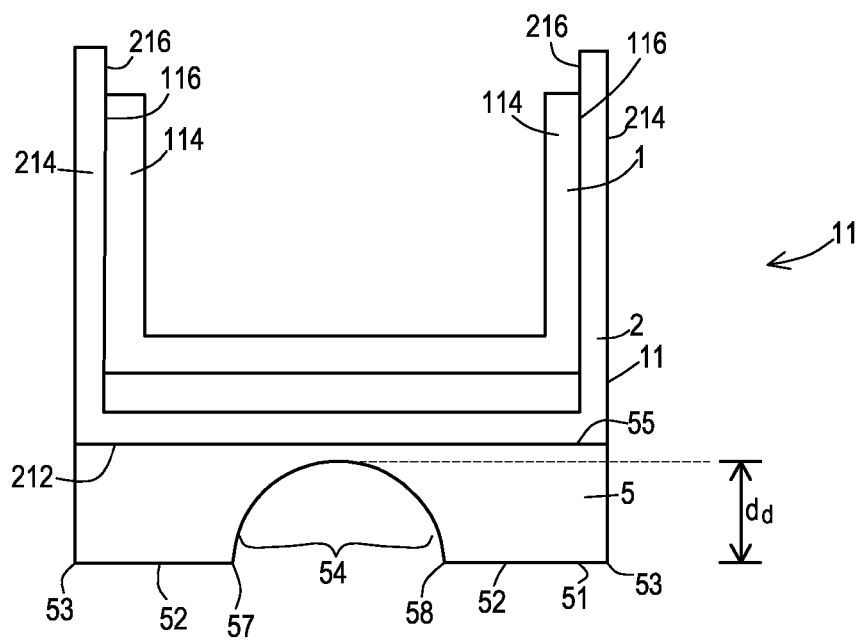
FIG. 2 depicts a side cross-sectional view of an exemplary first bone-engaging component of the exemplary ankle replacement device shown in FIG. 1.
Figure 3:
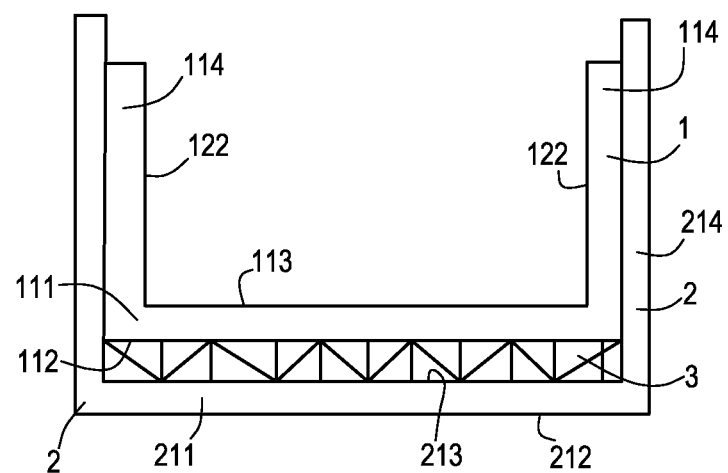
FIG. 3 depicts a side view of an exemplary bracket system suitable for use in the exemplary ankle replacement device shown in FIG. 1.
Figure 4:
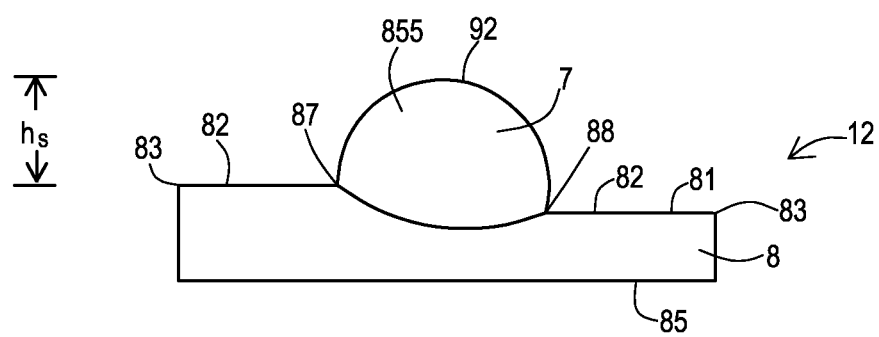
FIG. 4 depicts a side view of an exemplary second bone-engaging component of the exemplary ankle replacement device shown in FIG. 1.
Figure 5:
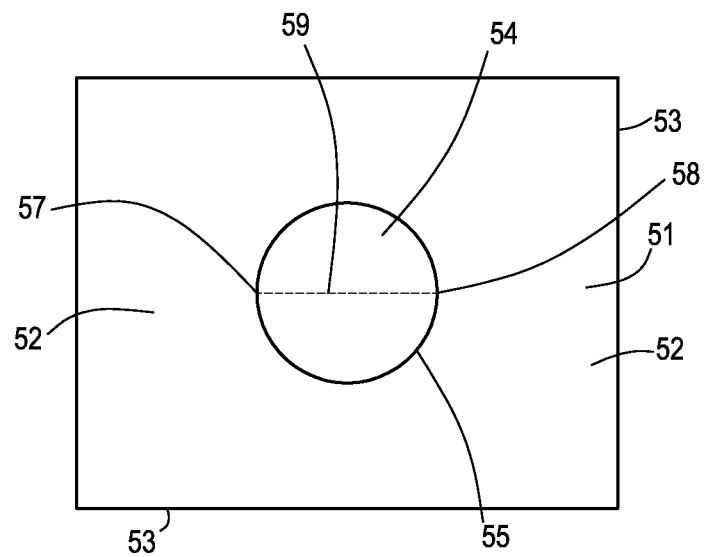
FIG. 5 depicts a bottom view of the exemplary first bone-engaging component shown in FIG. 2.
Figure 10:
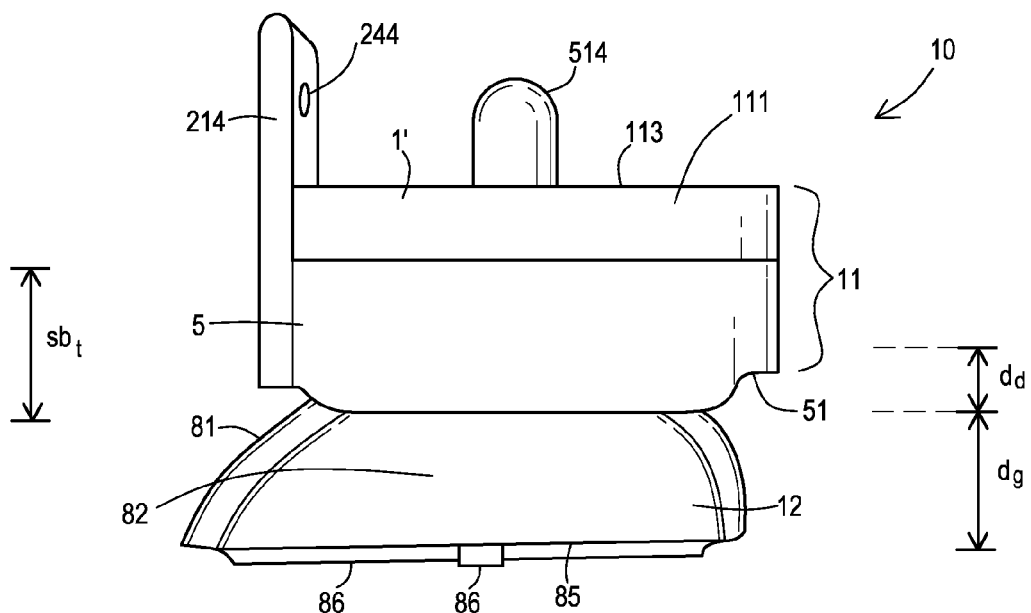
FIG. 10 depicts a side view of the exemplary ankle replacement device shown in FIG. 9.
Figure 11:
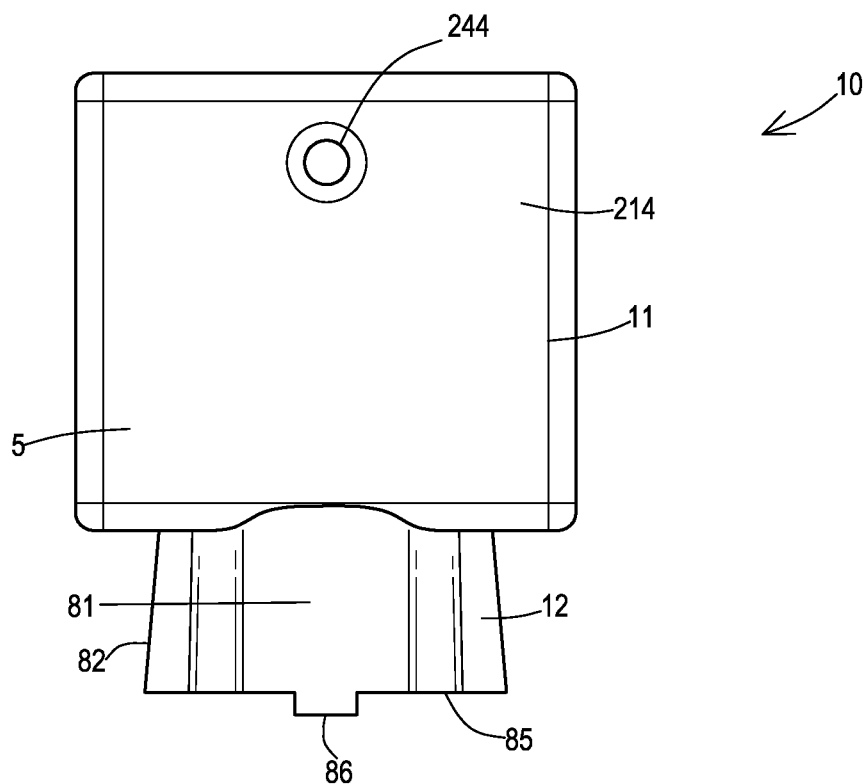
FIG. 11 depicts a view of the exemplary ankle replacement device shown in FIG. 10 as viewed from a left-hand side of FIG. 10.
Figure 12:
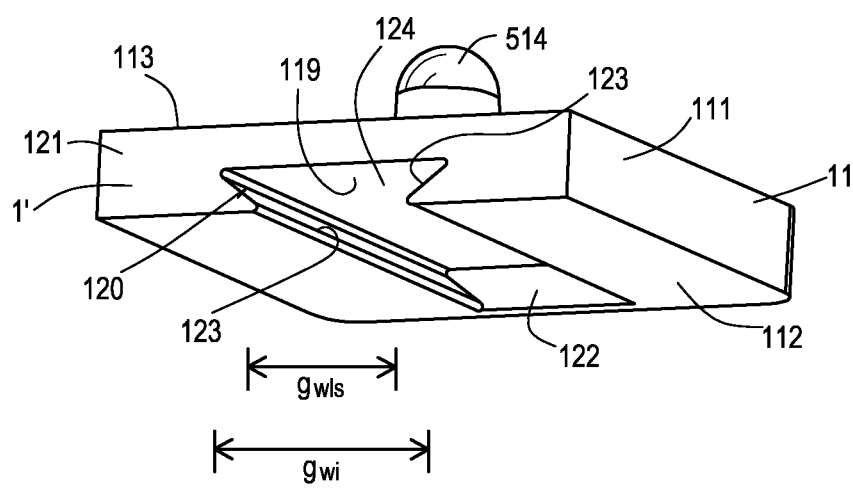
FIG. 12 depicts a profile view of an exemplary first bone-engaging component (also referred to herein as a first bracket) suitable for use in the exemplary ankle replacement device shown in FIG. 9.
Figure 13:
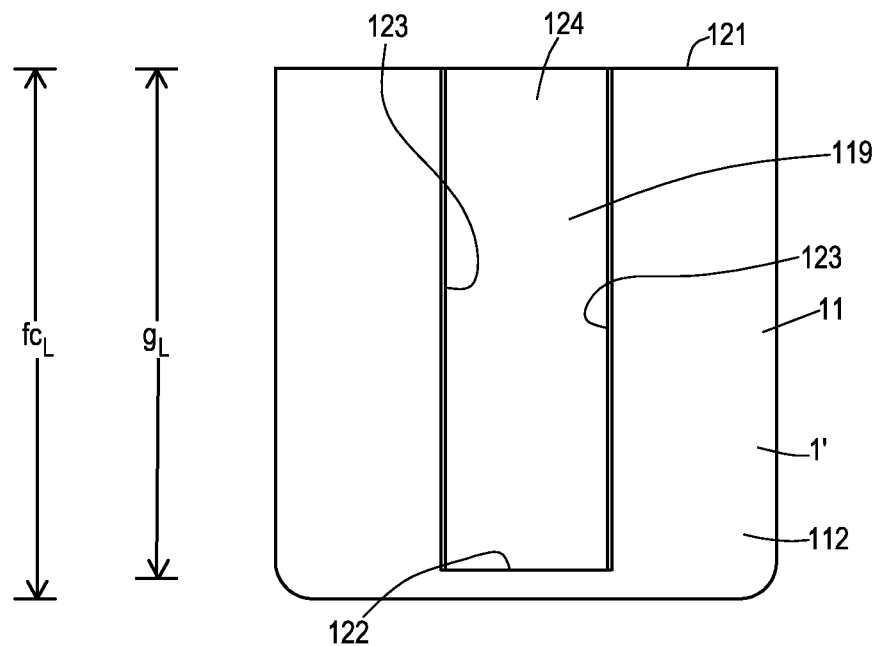
FIG. 13 depicts a view of a lower surface of the exemplary first bone-engaging component shown in FIG. 12.
Figure 14:
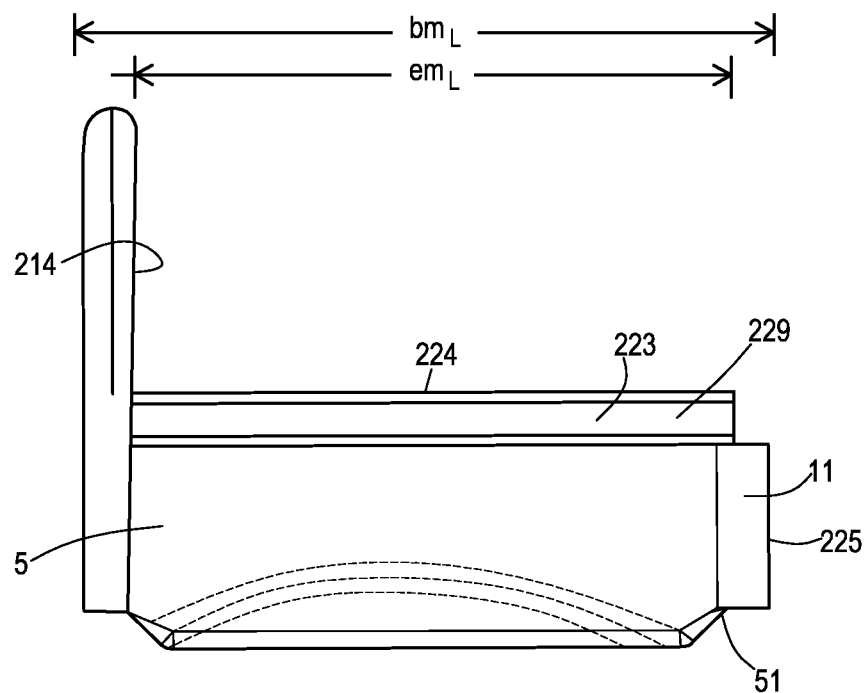
FIG. 14 depicts a side view of an exemplary supplemental first bone-engaging component (also referred to herein as a second bracket) suitable for use in the exemplary ankle replacement device shown in FIG. 9.
Figure 15A:
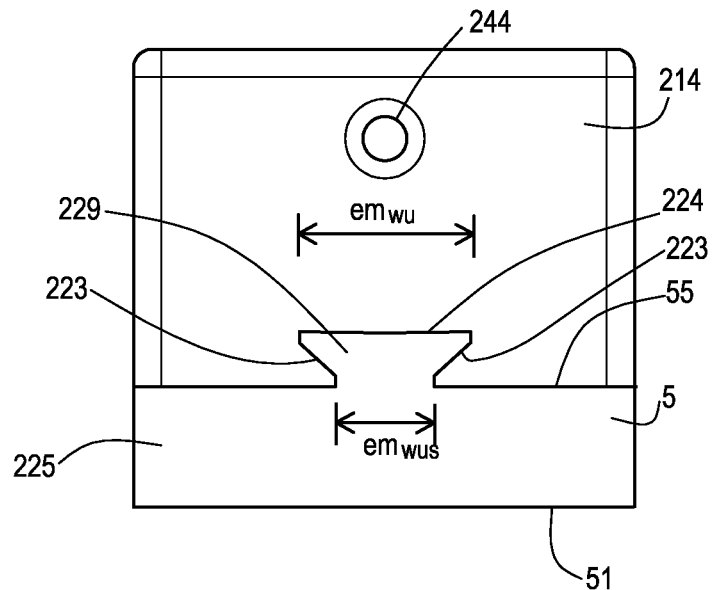
FIG. 15A depicts a view of the exemplary supplemental first bone-engaging component shown in FIG. 14 as viewed from a right-hand side of FIG. 14.
Figure 15B:
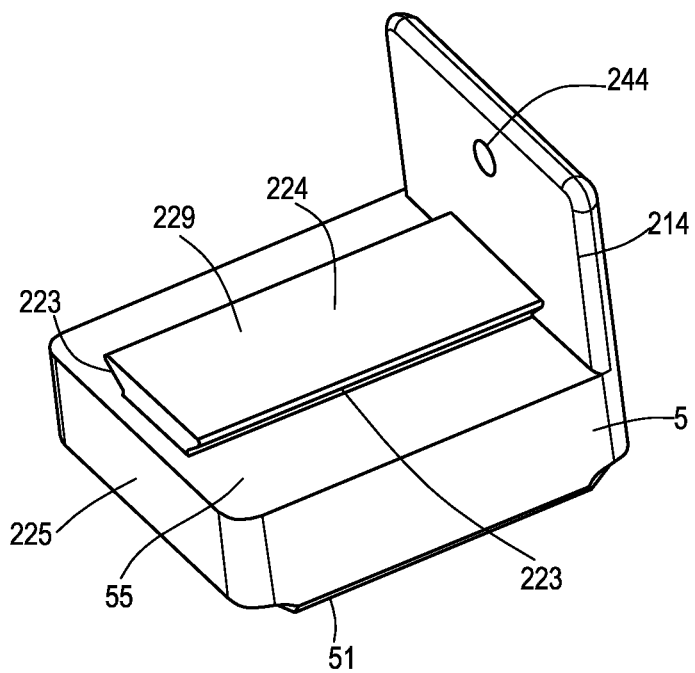
FIG. 15B depicts a profile view of the exemplary supplemental first bone-engaging component shown in FIG. 14.

The disclosed device features a lengthening/shortening mechanism on the tibial insertion bracket that allows the implementing physician to account for length discrepancies. This mechanism occurs by increasing or decreasing the space in between the two brackets using a locking mechanism. For example, as shown in FIG. 3, a specifically-sized spacer (i.e., spacer 3 shown in FIG. 3) made of a hard plastic may be inserted into the interbracket space in order to ensure optimum device stability and overall length (i.e., to account for length discrepancies). In other embodiments, such as shown in FIG. 10, a specifically-sized second bracket (i.e., second bracket 3 having a desired thickness, $sb_t$, as shown in FIG. 10) made of a hard plastic may be replaced (i.e., as needed, via a surgical procedure) in order to ensure optimum device stability and overall length (i.e., to account for length discrepancies).

In one desired embodiment, the disclosed device of the present invention allows the patient to have 360 degrees of motion, with inversion and eversion. In some embodiments, the disclosed device will have one or more of the following features: (i) a dorsiflexion component up to about 25 degrees characteristic, (ii) a plantarflexion component having up to about 50 degrees characteristic, (iii) an inversion component having about a 20 degree characteristic, (iv) an eversion component having about a 10 degree characteristic, (v) an internal rotation characteristic up to about 5 degrees (i.e., as used herein, "internal rotation" refers to rotation of a first bone-engaging component (or component thereof) in relation to a second bone-engaging component (i.e., the talar component, component 12) in the medial direction), and (vi) an external rotation characteristic up to about 6 degrees (i.e., as used herein, "external rotation" refers to rotation of a first bone-engaging component (or component thereof) in relation to a second bone-engaging component (i.e., the talar component, component 12) in the lateral direction). It must be noted that physiological range of motion varies for a given individual.

An established talar-tibial coupling joint will form greater support at the junction and prevent dislocations. By implementing an ellipsoid raised portion on the talar component coupled with the talar insertion cup on the tibial component, the range of motion will be strategically limited and the overall structure will form a stable connection at the joint (as shown in FIGS. 1-19).

Figure 9:
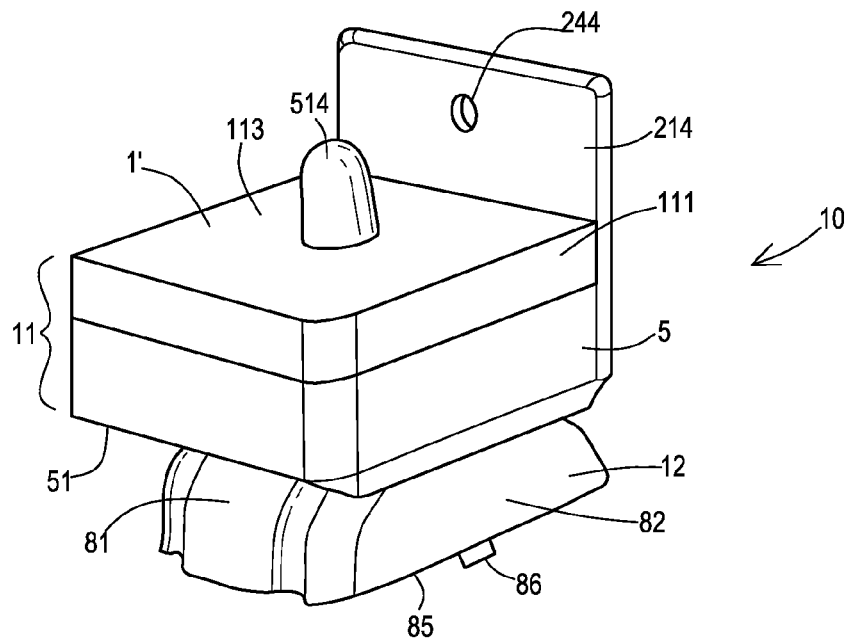
FIG. 9 depicts a profile view of another exemplary ankle replacement device of the present invention.

In some embodiments, two (2) tibial components, namely, the tibial bracket and the tibial attachment, have an integrated locking mechanism. As shown in FIGS. 9-10, the male-end of a flange on the tibial attachment is inserted into the corresponding resembling geometry female end of the tibial bracket and will rest in the integrated locking position that consists of material that remains at the end of the tibial bracket. The locking mechanism is completed by attachment of the tibial attachment to the first bone with bone-screw fixation. In some embodiments, the two (2) tibial components may be comprised of one or more of these locking mechanism areas, with the corresponding male and female ends being in the same corresponding direction per component, opposition of direction (one has male, one has female), or may encompass any combination of these for the ensured locking mechanism of these components.

In some embodiments, there is a potential for development of a mobile-bearing device, one that does not exhibit a locking mechanism and relies on the user's anatomy to apply physiological constant compression for stability of the device.

Figure 17:
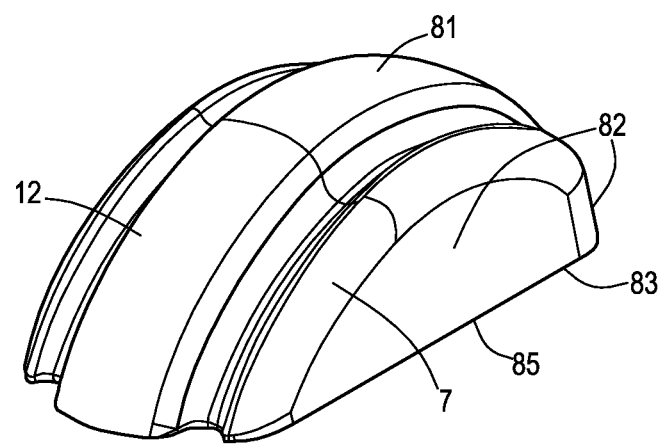
FIG. 17 depicts a profile view of an exemplary second bone-engaging component suitable for use in the exemplary ankle replacement device shown in FIG. 9.
Figure 18:
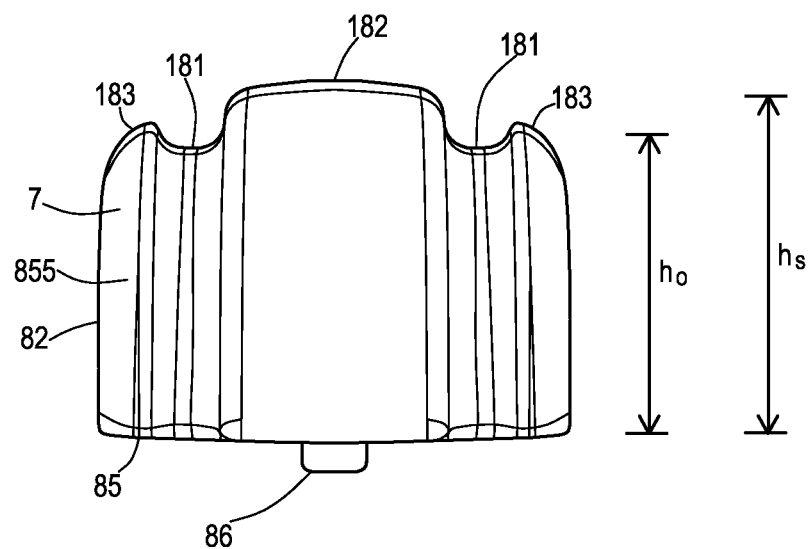
FIG. 18 depicts a frontal view of the exemplary second bone-engaging component shown in FIG. 17.
Figure 19:
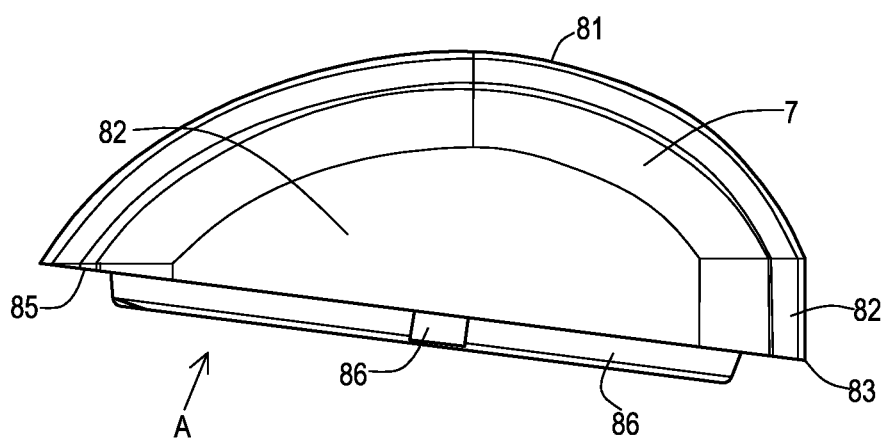
FIG. 19 depicts a side view of the exemplary second bone-engaging component shown in FIG. 17.
Figure 20:
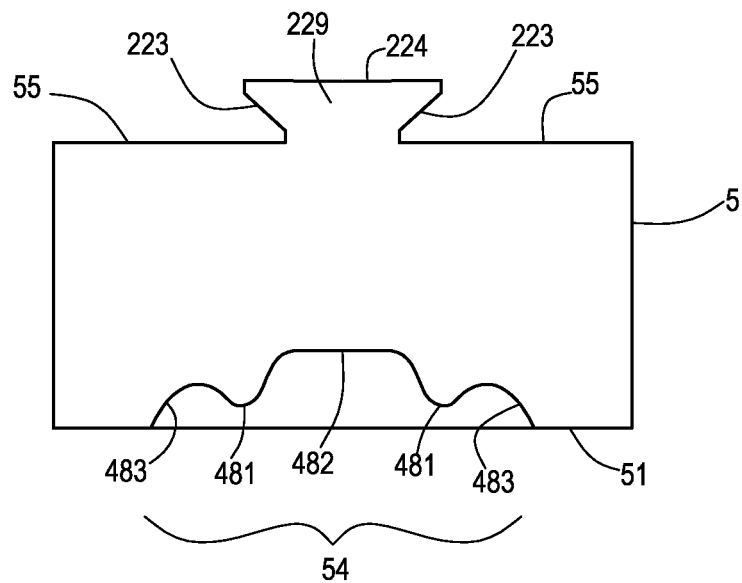
FIG. 20 depicts a cross-sectional view of the exemplary supplemental first bone-engaging component as view along line 20-20 as shown in FIG. 16.
Figure 21:
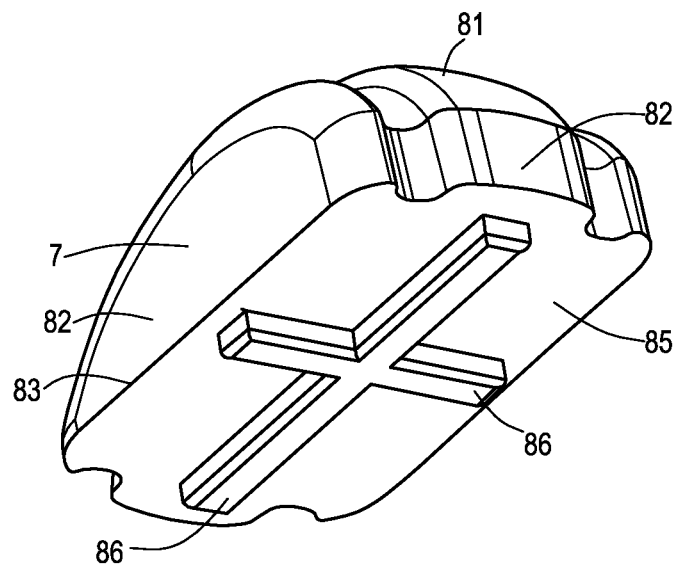
FIG. 21 depicts a view of the lower surface of the exemplary second bone-engaging component as view in direction A as shown in FIG. 19.

Further, in some embodiments, (i) the lower surface depression (i.e., lower surface depression 54) and (ii) the upper surface structure (i.e., upper surface structure 7) have have corresponding surface features that enable optimum connection therebetween. For example, as shown in FIGS. 17-19, upper surface 81 of upper surface structure 7 may comprise (1) at least two grooves 181 separated from one another and extending in a front to rear direction (i.e., a direction pointing from a person's heel to the person's toes) along upper surface 81, (2) a centrally-located track portion 182 between grooves 181, and (iii) outer track portions 183 on opposite outer portions of upper surface 81. As shown in FIGS. 17-19, centrally-located track portion 182 typically has a greater height (i.e., typically equal to $h_s$) compared to height $h_o$ of outer track portions 183 on opposite outer portions of upper surface 81 (see, FIG. 18).

Figure 16:
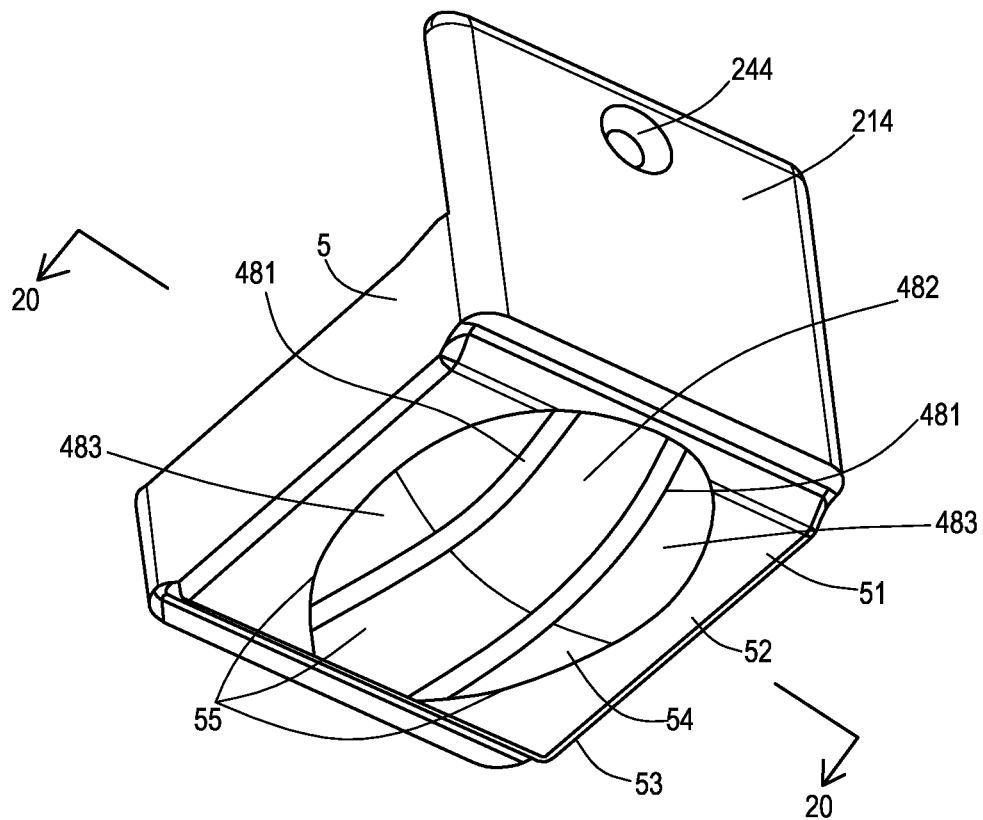
FIG. 16 depicts a view of the lower surface of the exemplary supplemental first bone-engaging component shown in FIG. 14.

As shown in FIG. 16, lower surface depression 54 of second bracket 2 of first base member 5 may comprise an interengaging surface configuration that corresponds to the surface configuration of upper surface 81 shown in FIGS. 17-19. For example, lower surface depression 54 may comprise (1) at least two rails 481 separated from one another and extending in a front to rear direction (i.e., a direction pointing from a person's heel to the person's toes) along lower surface depression 54 (i.e., so as to engage with two grooves 181 shown in FIGS. 17-19), (2) a centrally-located depression portion 482 between rails 481 (i.e., so as to contact/engage with centrally-located track portion 182 shown in FIGS. 17-19), and (iii) outer depression portions 483 on opposite outer portions of lower surface depression 54 (i.e., so as to contact/engage with outer track portions 183 shown in FIGS. 17-19).

Other Embodiments

Ankle Replacement Devices

1. An ankle replacement device 10 comprising: (I) a first bone-engaging component 11 operatively adapted to engage with a first bone (see, for example, first bone 810 in FIG. 22B), and comprising a first base member 5 comprising a lower surface 51, said lower surface 51 having an lower surface profile comprising (i) a lower surface portion 52 surrounded by a lower surface periphery 53, and (ii) a lower surface depression 54 surrounded by said lower surface portion 52, said lower surface depression 54 having a dome-shaped configuration with a depression depth, $d_d$, and a depression surface area 55 extending along said lower surface portion 52; and (II) a second bone-engaging component 12 operatively adapted to engage with a second bone (see, for example, second bone 811 in FIG. 22B), and comprising an upper surface 81, said upper surface 81 having an upper surface profile comprising (i) an upper surface portion 82 surrounded by an outer periphery 83, and (ii) an upper surface structure 7 surrounded by said outer periphery 83, said upper surface structure 7 having a dome-shaped configuration with a structure height, $h_s$, extending above said outer periphery 83 and a structure surface area 855 extending along said upper surface portion 82; said first bone-engaging component 11 being engagable with said second bone-engaging component 12 so that (i) at least a portion of said upper surface structure 7 is positionable within said lower surface depression 54, and (ii) when said portion of said upper surface structure 7 is positioned within said lower surface depression 54, said upper surface portion 81 is movable relative to said lower surface portion 51. As used herein, the phrase "dome-shaped configuration" refers to any three-dimensional shape/surface configuration having a curved outer surface portion. The "dome-shaped configuration" may comprise a substantially spherical shape/surface configuration (i.e., such as exemplary upper surface structure 7 shown in FIG. 1) or may comprise more of an ellipsoid shape/surface configuration (i.e., such as exemplary upper surface structure 7 shown in FIGS. 17-19).

2. The device 10 of embodiment 1, wherein each of said upper surface structure 7 and said lower surface depression 54 independently has an arch of curvature having an arch angle of greater than about 30° along any dissecting line thereof (or any angle value greater than 30°, in increments of 1°, or any range of angle values greater than 30°, e.g., about 45° to about 90°, in increments of 1°, along any dissecting line along lower surface depression 54 and/or about 110° to about 180°, in increments of 1°, along any dissecting line along upper surface structure 7). As used herein, the phrase "dissenting line" represents any line extending along upper surface structure 7 or lower surface depression 54 that dissects either upper surface structure 7 or lower surface depression 54. For example, see the dissecting line 59 extending from point 57 to point 58 along lower surface depression 54 in FIG. 5. See also, dissecting line 89 extending from point 87 to point 88 thru apex 92 along upper surface structure 7 in FIGS. 4 and 6.

3. The device 10 of embodiment 1 or 2, wherein said upper surface structure 7 has an arch of curvature having an arch angle ranging from about 135° to about 180° along any dissecting line thereof (or any angle value between about 135° to about 180°, in increments of 1°, or any range of angle values between about 135° to about 180°, e.g., about 165° to about 180°, in increments of 1°, along any dissecting line), and said lower surface depression 54 has an arch of curvature having an arch angle ranging from about 30° to about 180° along any dissecting line thereof (or any angle value between about 30° to about 180°, in increments of 1°, or any range of angle values between about 30° to about 180°, e.g., about 45° to about 60°, in increments of 1°, along any dissecting line).

4. The device 10 of any one of embodiments 1 to 3, wherein said upper surface structure 7 has an arch of curvature having an arch angle ranging from about 165° to about 180° along any dissecting line thereof (or any angle value between about 165° to about 180°, in increments of 1°, or any range of angle values between about 165° to about 180°, e.g., about 165° to about 180°, in increments of 1°, along any dissecting line), and said lower surface depression 54 has an arch of curvature having an arch angle ranging from about 30° to about 90° along any dissecting line thereof (or any angle value between about 30° to about 90°, in increments of 1°, or any range of angle values between about 30° to about 90°, e.g., about 45° to about 90°, in increments of 1°, along any dissecting line).

Figure 6:
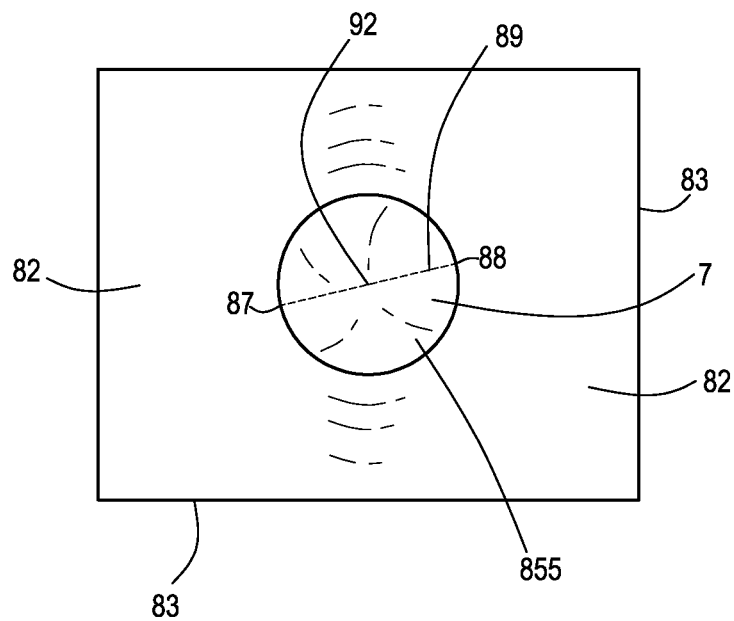
FIG. 6 depicts a top view of the exemplary second bone-engaging component shown in FIG. 4.
Figure 7A:
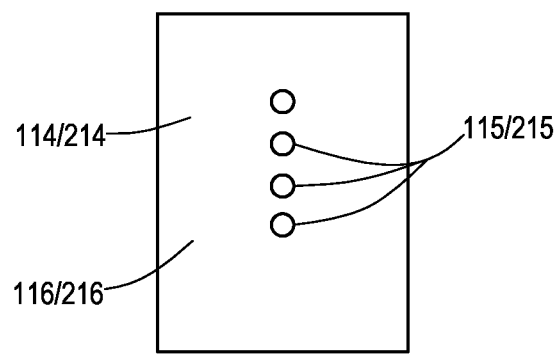
FIGS. 7A-7C depict suitable positioning members for use in the exemplary first and second brackets on the exemplary first bone-engaging component shown in FIGS. 1-3.
Figure 7B:
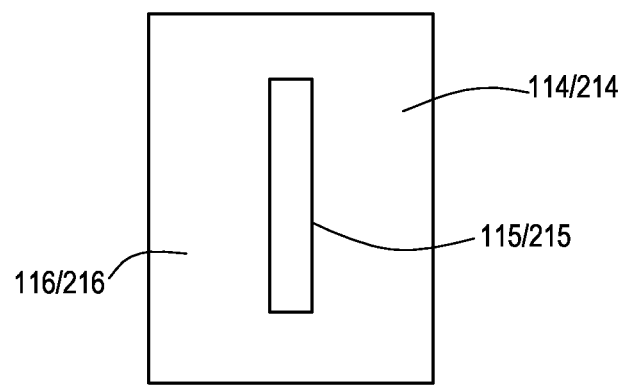
Figure 7C:
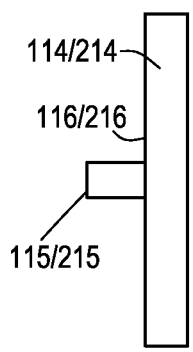

5. The device 10 of any one of embodiments 1 to 4, wherein each of said upper surface structure 7 and said lower surface depression 54 independently has an outer surface area, said lower surface depression 54 having a lower surface depression outer surface area that is less than an upper surface structure outer surface area of said upper surface structure 7. (Note, for example, the lower surface depression outer surface area comprises the surface area surrounded by circle 55 shown in FIG. 5, while the upper surface structure outer surface area comprises the outer surface area of upper surface structure 7 surrounded by upper surface portion 82 as shown in FIG. 6.)

6. The device 10 of any one of embodiments 1 to 5, wherein at least 60% of said lower surface depression outer surface area is in contact with said upper surface structure outer surface area.

7. The device 10 of any one of embodiments 1 to 6, wherein at least 80% of said lower surface depression outer surface area is in contact with said upper surface structure outer surface area.

8. The device 10 of any one of embodiments 1 to 7, wherein about 100% of said lower surface depression outer surface area is in contact with said upper surface structure outer surface area.

9. The device 10 of any one of embodiments 1 to 8, wherein, when said first bone-engaging component 11 is engaged with said second bone-engaging component 12, portions of said upper surface portion 82 are either in contact with corresponding portions of said lower surface portion 52 or spaced from corresponding portions of said lower surface portion 52 by a distance ranging from greater than 0 to about 5.0 cm (more typically, from greater than 0 to about 2.0 cm). See, for example, the distance, $d_g$, of the gap 31 shown in FIG. 1. See also, the distance, $d_g$, of the "gap" between lower surface 51 of first base member 5 and lower surface 85 of second bone-engaging component 12 as shown in FIG. 10.

10. The device 10 of any one of embodiments 1 to 9, wherein said device 10 allows a patient (not shown) to have 360° of motion with inversion and eversion.

11. The device 10 of any one of embodiments 1 to 10, wherein said device 10 provides an inversion characteristic of up to about 25° (or any value or range from greater than 0° to about 25°, in increments of 1°, e.g., 20° or from 15° to 21°) and an eversion characteristic of up to about 15° (or any value or range from greater than 0° to about 15°, in increments of 1°, e.g., 10° or from 5° to 9°).

12. The device 10 of any one of embodiments 1 to 11, wherein said device 10 provides a dorsiflexion characteristic of up to about 25° (or any value or range from greater than 0° to about 25°, in increments of 1°, e.g., 25° or from 8° to 25°), and a plantarflexion characteristic of up to about 50° (or any value or range from greater than 0° to about 50°, in increments of 1°, e.g., 25° or from 24° to 50°).

13. The device 10 of any one of embodiments 1 to 12, wherein each of said first base member 5 and said second base member 8 independently has a base member thickness of from about 0.5 centimeter (cm) to about 2.0 cm.

14. The device 10 of any one of embodiments 1 to 13, wherein each of said first bone-engaging component 11 and said second bone-engaging component 11 independently has a thickness of from about 0.5 cm to about 3.0 cm (more typically, from about 0.5 cm to about 2.0 cm).

15. The device 10 of any one of embodiments 1 to 14, wherein said first bone-engaging component 11 further comprises a first bracket 1 sized and operatively adapted to be attached to a first bone (see, for example, first bone 810 in FIG. 22B), said first bracket 1 comprising a first bracket base 111, a first bracket base lower surface 112, a first bracket base upper surface 113, and at least one first bracket side wall 114 extending upward from said first bracket base upper surface 113.

16. The device 10 of embodiment 15, wherein said first bone-engaging component 11 further comprises a second bracket 2 sized and operatively adapted to be attached to said first bracket 1 and said first base member 5, said second bracket 2 comprising a second bracket base 211, a second bracket base lower surface 212, a second bracket base upper surface 213, and at least one second bracket side wall 214 extending upward from said second bracket base upper surface 213.

Figure 8A:
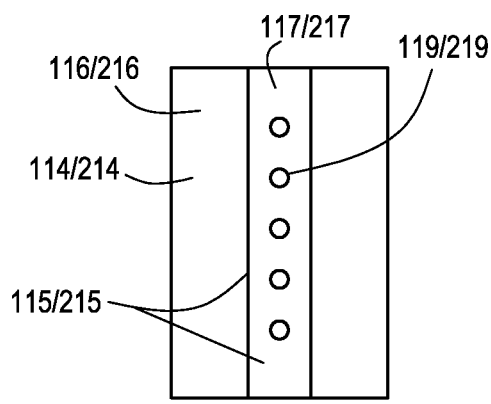
FIGS. 8A-8D depict additional suitable positioning members for use in the exemplary first and second brackets on the exemplary first bone-engaging component shown in FIGS. 1-3.
Figure 8B:
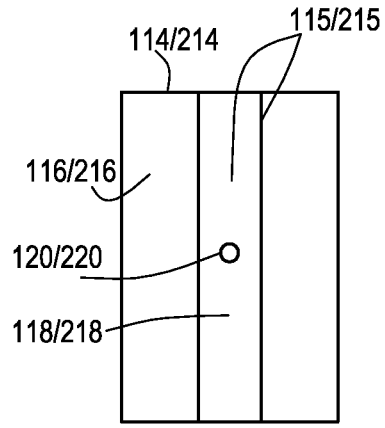
Figure 8C:
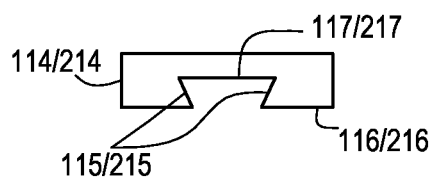
Figure 8D:
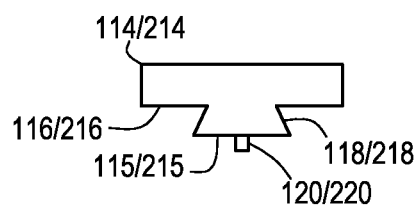

17. The device 10 of embodiment 15 or 16, wherein said at least one first bracket side wall 114, said at least one second bracket side wall 214 or both comprises a positioning member 115/215 therein, said positioning member 115/215 enabling said first bracket 1 to be (i) engaged with and (ii) movable relative to said second bracket 2 such that said first bracket lower surface 112 moves away from or towards said second bracket upper surface 213. See, for example, possible positioning members 115 and/or 215 shown in FIGS. 7A-8D. Any one or all of said at least one first bracket side wall 114, said at least one second bracket side wall 214 or both may have any one of positioning members 115 and/or 215 shown in FIGS. 7A-8D so as to enable first bracket 1 to engage with second bracket 2. As shown in FIGS. 8A-8C, in some embodiments, first bracket side wall 114 may comprise connecting surface 116 and second bracket side wall 214 may comprise corresponding connecting surface 216 with connecting surface 116 further comprising female groove 117 and holes 119, and corresponding connecting surface 216 comprising male connector 218 with mechanical fastener 220 (or connecting surface 116 further comprising male connector 118 with mechanical fastener 120 and corresponding connecting surface 216 comprising female groove 217 and holes 219). Mechanical fastener 120/220 may comprise, for example, a screw, a peg, etc. Holes 119/219 may be present in any number and may be spaced in any configuration. In some embodiments, holes 119/219 are present in an amount of about 5 (or any number or range between 1 and 10 in increments of 1) holes 119/219 and are spaced about 1 centimeter (cm) from each other.

18. The device 10 of any one of embodiments 15 to 17, wherein said first bone-engaging component 11 further comprises a locking mechanism (not shown), said locking mechanism enabling said first bracket 1 to be locked in place relative to said second bracket 2. Any locking mechanism may be used, typically, in combination with positioning members 115 and/or 215 shown in FIGS. 7A-8D, to lock first bracket 1 with second bracket 2. Suitable locking mechanism may include, but are not limited to, screws, mechanical latching, etc.

19. The device 10 of any one of embodiments 15 to 18, wherein said first bone-engaging component 11 further comprises a spacer 3 sized so as to be positionable between said first bracket lower surface 112 and said second bracket upper surface 213.

20. The device 10 of any one of embodiments 15 to 19, wherein said second bracket lower surface 212 is attached to an upper surface 55 of said first base member 5.

21. The device 10 of any one of embodiments 1 to 9 and 12 to 14, wherein said first bone-engaging component 11 further comprises a first bone attachment component 1' sized and operatively adapted to be attached to a first bone (see, for example, first bone 810 in FIG. 22B), said first bone attachment component 1' comprising a first component base 111, a first component base lower surface 112, a first component base upper surface 113, and at least one first component protruding member 514 extending upward from said first component base upper surface 113.

22. The device 10 of embodiment 21, wherein said first base member 5 further comprises (i) a base member upper surface 55, and (ii) at least one base member bracket side wall 214 extending upward from said base member upper surface 55.

23. The device 10 of embodiment 22, wherein said at least one base member bracket side wall 214 comprises a single base member bracket side wall 214 and further comprises a bone-connecting hole 244 extending through said single base member bracket side wall 214.

24. The device 10 of any one of embodiments 21 to 23, wherein said first bone-engaging component 11 further comprises a locking mechanism, said locking mechanism enabling said first bone attachment component 1' to be locked in place relative to said first base member 5 (i.e., interengaged with one another so as to not move relative to one another). Any locking mechanism may be used to lock first bone attachment component 1' with first base member 5. Suitable locking mechanism may include, but are not limited to, screws, mechanical latching, etc.

25. The device 10 of any one of embodiments 21 to 24, wherein said first component base lower surface 112 comprises an engaging groove 119 therein (see, FIGS. 12-13), and said base member upper surface 55 comprises a corresponding engaging member 229 extending along said base member upper surface 55.

26. The device 10 of embodiment 25, wherein said engaging groove 119 has (i) a groove width, $g_{wls}$, along said first component base lower surface 112, and (ii) a groove width, $g_{wi}$, positioned between said first component base lower surface 112 and said first component base upper surface 113, and said groove width, $g_{wls}$, along said first component base lower surface 112 is less than said a groove width, $g_{wi}$, positioned between said first component base lower surface 112 and said first component base upper surface 113.

27. The device 10 of embodiment 25 or 26, wherein said engaging groove 119 has a groove length, $g_L$, along said first component base lower surface 112, said groove length, $g_L$, along said first component base lower surface 112 being less than an overall length, $fc_L$, of said first bone attachment component 1'. See, for example, FIG. 13.

28. The device 10 of any one of embodiments 24 to 27, wherein said engaging groove 119 has a groove entrance 120 along a side surface 121 of said first bone attachment component 1' and a groove end wall 122 opposite said groove entrance 120. See, for example, FIG. 12.

29. The device 10 of any one of embodiments 24 to 28, wherein said engaging groove 119 has (i) opposite groove side walls 123, and (ii) a groove upper surface 124 extending between said opposite groove side walls 123. See, for example, FIG. 12.

30. The device 10 of any one of embodiments 24 to 29, wherein said corresponding engaging member 229 has (i) a engaging member width, $em_{wus}$, along said base member upper surface 55, and (ii) a engaging member width, $em_{wu}$, positioned away from said base member upper surface 55, and said engaging member width, $em_{wu}$, positioned away from said base member upper surface 55 is greater than engaging member width, $em_{wus}$, along said base member upper surface 55. See, for example, FIG. 15.

31. The device 10 of embodiment 30, wherein said corresponding engaging member 229 has an engaging member length, $em_L$, along said base member upper surface 55, said engaging member length, $em_L$, along said base member upper surface 55 being less than an overall length, $bm_L$, of said first base member 5. See, for example, FIG. 14. Typically, engaging member length, $em_L$, along base member upper surface 55 is less than a length extending from (i) at least one base member bracket side wall 214 to an opposite side surface 225 of said first base member 5. See, for example, FIG. 14.

32. The device 10 of embodiment 30 or 31, wherein said corresponding engaging member 229 has (i) opposite engaging member side walls 223, and (ii) an engaging member upper surface 224 extending between said opposite engaging member side walls 223. See, for example, FIGS. 14-15B.

33. The device 10 of any one of embodiments 1 to 32, wherein said second bone-engaging component 12 further comprises a lower surface 85, at least a portion of which is sized and operatively adapted to be attached to a second bone (see, for example, second bone 811 in FIG. 22B).

34. The device 10 of any one of embodiments 1 to 33, wherein said second bone-engaging component 12 further comprises a lower surface 85 and a bone-connecting member 86 along said lower surface 85, said bone-connecting member being operatively adapted to attach to a second bone.

35. The device 10 of embodiment 34, wherein said bone-connecting member 86 comprises two or more surface projections 86 extending out from said lower surface 85.

36. The device 10 of embodiment 34 or 35, wherein said bone-connecting member 86 comprises two surface projections 86 extending out from said lower surface 85, said two surface projections 86 intersecting with one another along said lower surface 85.

37. The device 10 of any one of embodiments 34 to 36, wherein said bone-connecting member 86 comprises two surface projections 86 extending out from said lower surface 85, said two surface projections 86 intersecting with one to form a cross-shape along said lower surface 85.

38. The device 10 of any one of embodiments 1 to 37, wherein said lower surface depression 54 and said upper surface 81 of said upper surface structure 7 have corresponding surface features that enable optimum connection therebetween. See, for example, FIGS. 16-19.

39. The device 10 of any one of embodiments 1 to 38, wherein said upper surface structure 7 comprise (1) at least two grooves 181 separated from one another and extending in a front to rear direction (i.e., a direction pointing from a person's heel to the person's toes) along upper surface 81, (2) a centrally-located track portion 182 between grooves 181, and (3) outer track portions 183 on opposite outer portions of upper surface 81. As shown in FIGS. 17-19, centrally-located track portion 182 typically has a greater height (i.e., typically equal to $h_s$) compared to height $h_o$ of outer track portions 183 on opposite outer portions of upper surface 81 (see, FIG. 18). Further, it should be noted that each of (1) at least two grooves 181, (2) a centrally-located track portion 182, and (3) outer track portions 183 may have surface features that maximize surface contact between said lower surface depression 54 and said upper surface 81 of said upper surface structure 7. In some embodiments, one or more of (1) at least two grooves 181, (2) a centrally-located track portion 182, and (3) outer track portions 183 may have surface features that interlock lower surface depression 54 of said first base member 5 and said upper surface 81 of said upper surface structure 7 so as to be in an interlocked, movably slidable configuration relative to one another.

40. The device 10 of any one of embodiments 1 to 39, wherein said lower surface depression 54 of said first base member 5 comprises (1) at least two rails 481 separated from one another and extending in a front to rear direction (i.e., a direction pointing from a person's heel to the person's toes) along lower surface depression 54 (i.e., so as to engage with two grooves 181 shown in FIGS. 17-19), (2) a centrally-located depression portion 482 between rails 481 (i.e., so as to contact/engage with centrally-located track portion 182 shown in FIGS. 17-19), and (3) outer depression portions 483 on opposite outer portions of lower surface depression 54 (i.e., so as to contact/engage with outer track portions 183 shown in FIGS. 17-19).

41. The device 10 of any one of embodiments 1 to 40, wherein said first bone-engaging component 11 and said second bone-engaging component 12 each independently comprise a titanium alloy cobalt-chromium alloy, or a polymeric material.

42. The device 10 of any one of embodiments 1 to 41, wherein said first bone-engaging component 11 and said second bone-engaging component 12 each independently comprise a polyethylene (e.g., an ultra-high molecular weight polyethylene (UHMWPE) or any other polymeric material (e.g., any suitable biocompatible polymeric material).

43. The device 10 of any one of embodiments 16 to 20, wherein said first and second brackets 1 and 2 each independently comprise a titanium alloy comprising Ti-6Al-4V or any other biocompatible titanium alloy, and said first and second base members 5 and 8 each independently comprise a polyethylene.

44. The device 10 of any one of embodiments 21 to 42, wherein said first bone attachment component 1' and said second bone-engaging component 12 each independently comprise a titanium alloy comprising Ti-6Al-4V or any other biocompatible titanium alloy, and said first base member 5 comprises a polyethylene.

45. The device 10 of any one of embodiments 1 to 44, wherein said first bone-engaging component 11 is engaged with said second bone-engaging component 12.

46. The device 10 of any one of embodiments 1 to 45, wherein said first bone-engaging component 11 is connected to the first bone, and said second bone-engaging component 12 is connected to the second bone.

Figure 22A:
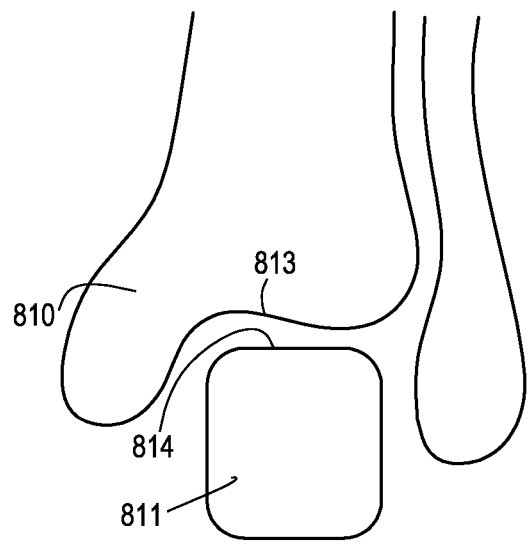
FIG. 22A depicts a view of a tibia bone and a talia bone of an ankle prior to insertion of the exemplary ankle replacement device shown in FIG. 9 into the ankle joint.
Figure 22B:
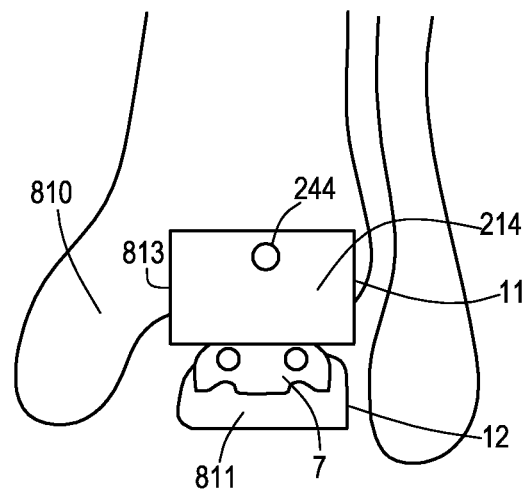
FIG. 22B depicts a view of a tibia bone and a talia bone of an ankle after insertion of the exemplary ankle replacement device shown in FIG. 9 into the ankle joint.

47. The device 10 of any one of embodiments 1 to 46, wherein said first bone-engaging component 11 is connected to the first bone, the first bone comprising a tibia bone, said second bone-engaging component 12 is connected to a second bone, and the second bone comprising a talar bone. As shown in FIG. 22B, a tibia bone (i.e., tilia bone 810) could be attached/connected (directly or indirectly) to inner surface 122 of first bone-engaging component 11 or to first bracket base upper surface 113 so that first component protruding member 514 extends into the tilia bone and/or to base member bracket side wall 214 via, for example, a screw extending through bone-connecting hole 244 and said single base member bracket side wall 214. See, for example, FIGS. 1 and 9. Further, as shown in FIG. 22B, the talar bone (i.e., talar bone 811) could be attached/connected (directly or indirectly) to lower surface 85 of second bone-engaging component 12. See, for example, FIGS. 1 and 9.

Methods of Making Ankle Replacement Devices:

48. A method of making the device 10 of any one of embodiments 1 to 47, said method comprising: forming the first bone-engaging component 11; and forming the second bone-engaging component 12.

49. The method of embodiment 48, said forming the first bone-engaging component 11 comprising: forming the first base member 5; forming the first bracket 1 or the first bone attachment component 1'; and optionally forming the second bracket 2.

50. The method of embodiment 48 or 49, said forming the second bone-engaging component 12 comprising forming the second base member 8.

51. The method of any one of embodiments 48 to 50, wherein each of said forming steps comprises a thermoforming step.

52. The method of any one of embodiments 48 to 51, further comprising: assembling the first bone-engaging component 11 and the second bone-engaging component 12 with one another so that (i) that at least a portion of the upper surface structure 7 is positioned within the lower surface depression 54, and (ii) the upper surface portion 81 is movable relative to the lower surface portion 51.

Methods of Using Ankle Replacement Devices:

53. A method of using the device 10 of any one of embodiments 1 to 47, said method comprising: implanting the first bone-engaging component 11 and the second bone-engaging component 12 into a patient (not shown). See, for example, FIGS. 22A and 22B, which depict an ankle joint before and after the device 10 of the present invention is surgically inserted into the ankle joint. Although not shown in the figures, it should be understood that during insertion, portions 813 of tibia bone 810 and portions 814 of talar bone 811 are typically removed to provide a bone surface that accommodates surface structures (e.g., first component protruding member 514, first bracket base upper surface 113, and/or bone-connecting member 86) along outer, bone-connecting surfaces of the first bone-engaging component 11 and the second bone-engaging component 12.

54. The method of embodiment 53, further comprising: attaching the first bone-engaging component 11 to a first bone 810; and attaching the second bone-engaging component 12 to a second bone 811.

55. A method of using the device 10 of any one of embodiments 1 to 47, said method comprising: attaching the first bone-engaging component 11 to a first bone 810; and attaching the second bone-engaging component 12 to a second bone 811.

56. A method of using the device 10 of any one of embodiments 1 to 47, said method comprising: unlocking a locking mechanism of the device 10 so that the first bone-engaging component 11 and the second bone-engaging component 12 are movable relative to one another; adjusting an overall length of the device 10; and locking the locking mechanism of the device 10 so that the first bone-engaging component 11 is in a fixed position relative to the second bone-engaging component 12.

57. A method of any one of embodiments 53 to 56, said method comprising: inserting a spacer 3 within the first bone-engaging component 11.

58. A method of any one of embodiments 53 to 57, said method comprising: replacing (i) a used spacer 3 with a new spacer 3 or (ii) a used first base member 5 with a new first base member 5 within the first bone-engaging component 11.

59. A method of any one of embodiments 53 to 58, said method comprising: replacing a used first base member 5 with a new first base member 5, the new first base member 5 having an overall height (i.e., thickness) greater than the used first base member 5 (i.e., to accommodate for a change in leg length over time).

60. A method of any one of embodiments 53 to 58, said method comprising: replacing a used first base member 5 with a new first base member 5, the new first base member 5 having an overall height (i.e., thickness) less than the used first base member 5 (i.e., to accommodate for a change in leg length over time).

61. The method of any one of embodiments 53 to 60, wherein the first bone-engaging component 11 is connected to a tibia bone 810, and the second bone-engaging component 12 is connected to a talar bone 811.

62. The method of any one of embodiments 53 to 61, wherein the device 10 replaces an ankle of the patient.

EXAMPLES

Example 1

Manufacture of Ankle Replacement Devices

Ankle replacement devices, similar to devices 10 shown in FIGS. 1-21, were prepared, and surgically inserted as shown in FIG. 22B.

It should be understood that although the above-described ankle replacement devices, kits, and methods are described as "comprising" one or more components or steps, the above-described ankle replacement devices, kits, and methods may "comprise," "consists of," or "consist essentially of" any of the above-described components, features or steps of the ankle replacement devices, kits, and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a device, a kit, and/or method that "comprises" a list of elements (e.g., components, features or steps) is not necessarily limited to only those elements (or components or steps), but may include other elements (or components or steps) not expressly listed or inherent to the device, kit, and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a device, a kit, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described ankle replacement devices, kits, and methods may comprise, consist essentially of, or consist of any of the herein-described components and features, as shown in the figures with or without any feature(s) not shown in the figures. In other words, in some embodiments, the ankle replacement devices, kits, and/or methods of the present invention do not have any additional features other than those shown in the figures, and such additional features, not shown in the figures, are specifically excluded from the ankle replacement devices, kits, and/or methods. In other embodiments, the ankle replacement devices, kits, and/or methods of the present invention do have one or more additional features that are not shown in the figures.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An ankle replacement device comprising:
   (I) a first bone-engaging component operatively adapted to engage with a first bone, and comprising (1) a first base member comprising (a) a lower surface, said lower surface having an lower surface profile comprising (i) a lower surface portion surrounded by a lower surface periphery, and (ii) a lower surface depression surrounded by said lower surface portion, said lower surface depression having a dome-shaped configuration with a depression depth, $d_d$, and a depression surface area extending along said lower surface portion, (b) a base member upper surface, and (c) at least one base member bracket side wall extending upward from said base member upper surface; and (2) a first bone attachment component sized and operatively adapted to be attached to the first bone, said first bone attachment component comprising a first component base, a first component base lower surface, a first component base upper surface, and at least one first component protruding member extending upward from said first component base upper surface, said first component base lower surface comprising an engaging groove therein, and said base member upper surface comprising a corresponding engaging member extending along said base member upper surface, said engaging groove and said corresponding engaging member being engagable with one another so as to engage said first bone attachment component with said first base member; and
   (II) a second bone-engaging component operatively adapted to engage with a second bone, and comprising an upper surface, said upper surface having an upper surface profile comprising (i) an upper surface portion surrounded by an outer periphery, and (ii) an upper surface structure surrounded by said outer periphery, said upper surface structure having a dome-shaped configuration with a structure height, $h_s$, extending above said outer periphery and a structure surface area extending along said upper surface portion;
   said first bone-engaging component being engagable with said second bone-engaging component so that (i) at least a portion of said upper surface structure is positionable within said lower surface depression, and (ii) when said portion of said upper surface structure is positioned within said lower surface depression, said upper surface portion is movable relative to said lower surface portion;
   wherein said upper surface structure comprises (1) at least two grooves separated from one another and extending in a front to rear direction along said upper surface, (2) a centrally-located track portion between said at least two grooves, and (3) outer track portions on opposite outer portions of said upper surface; and said lower surface depression of said first base member comprises (1) at least two rails separated from one another and extending in said front to rear direction along said lower surface depression so as to engagable with said at least two grooves, (2) a centrally-located depression portion between at least two rails so as to contact/engage with said centrally-located track portion, and (3) outer depression portions on opposite outer portions of said lower surface depression, and
   wherein said at least one base member bracket side wall comprises a single base member bracket side wall and further comprises a bone-connecting hole extending through said single base member bracket side wall.

2. The ankle replacement device of claim 1, wherein said upper surface structure comprises two grooves separated from one another and extending in said front to rear direction along said upper surface; and said lower surface depression of said first base member comprises two rails separated from one another and extending in said front to rear direction along said lower surface depression.

3. The ankle replacement device of claim 1, wherein said engaging groove has (i) a groove width, $g_{wls}$, along said first component base lower surface, and (ii) a groove width, $g_{wi}$, positioned between said first component base lower surface and said first component base upper surface, and said groove width, $g_{wls}$, along said first component base lower surface is less than said groove width, $g_{wi}$, positioned between said first component base lower surface and said first component base upper surface; and said corresponding engaging member has (i) a engaging member width, $em_{wus}$, along said base member upper surface, and (ii) a engaging member width, $em_{wu}$, positioned away from said base member upper surface, and said engaging member width, $em_{wu}$, positioned away from said base member upper surface is greater than said engaging member width, $em_{wus}$, along said base member upper surface.

4. The ankle replacement device of claim 3, wherein said engaging groove has (a) a groove length, $g_L$, along said first component base lower surface, said groove length, $g_L$, along said first component base lower surface being less than an overall length, $fc_L$, of said first bone attachment component, (b) a groove entrance along a side surface of said first bone attachment component, and (c) a groove end wall opposite said groove entrance; and said corresponding engaging member has an engaging member length, $em_L$, along said base member upper surface, said engaging member length, $em_L$, along said base member upper surface being less than an overall length, $bm_L$, of said first base member.

5. The ankle replacement device of claim 1, wherein each of said first bone-engaging component and said second bone-engaging component independently has an overall thickness of from about 0.5 centimeter (cm) to about 3.0 cm.

6. An ankle replacement device comprising:
   (I) a first bone-engaging component operatively adapted to engage with a first bone, and comprising (1) a first base member comprising (a) a lower surface, said lower surface having an lower surface profile comprising (i) a lower surface portion surrounded by a lower surface periphery, and (ii) a lower surface depression surrounded by said lower surface portion, said lower surface depression having a dome-shaped configuration with a depression depth, $d_d$, and a depression surface area extending along said lower surface portion, (b) a base member upper surface, and (c) at least one base member bracket side wall extending upward from said base member upper surface; and (2) a first bone attachment component sized and operatively adapted to be attached to the first bone, said first bone attachment component comprising a first component base, a first component base lower surface, a first component base upper surface, and at least one first component protruding member extending upward from said first component base upper surface, said first component base lower surface comprising an engaging groove therein, and said base member upper surface comprising a corresponding engaging member extending along said base member upper surface, said engaging groove and said corresponding engaging member being engagable with one another so as to engage said first bone attachment component with said first base member; and (II) a second bone-engaging component operatively adapted to engage with a second bone, and comprising an upper surface, said upper surface having an upper surface profile comprising (i) an upper surface portion surrounded by an outer periphery, and (ii) an upper surface structure surrounded by said outer periphery, said upper surface structure having a dome-shaped configuration with a structure height, $h_s$, extending above said outer periphery and a structure surface area extending along said upper surface portion;

said first bone-engaging component being engagable with said second bone-engaging component so that (i) at least a portion of said upper surface structure is positionable within said lower surface depression, and (ii) when said portion of said upper surface structure is positioned within said lower surface depression, said upper surface portion is movable relative to said lower surface portion, and wherein said at least one base member bracket side wall comprises a single base member bracket side wall and further comprises a bone-connecting hole extending through said single base member bracket side wall.

7. The ankle replacement device of claim 6, wherein said engaging groove has (i) a groove width, $g_{wls}$, along said first component base lower surface, and (ii) a groove width, $g_{wi}$, positioned between said first component base lower surface and said first component base upper surface, and said groove width, $g_{wls}$, along said first component base lower surface is less than said groove width, $g_{wi}$, positioned between said first component base lower surface and said first component base upper surface; and said corresponding engaging member has (i) a engaging member width, $em_{wus}$, along said base member upper surface, and (ii) a engaging member width, $em_{wu}$, positioned away from said base member upper surface, and engaging member width, $em_{wu}$, positioned away from said base member upper surface is greater than said engaging member width, $em_{wus}$, along said base member upper surface.

8. The ankle replacement device of claim 7, wherein said engaging groove has (a) a groove length, $g_L$, along said first component base lower surface, said groove length, $g_L$, along said first component base lower surface being less than an overall length, $fc_L$, of said first bone attachment component, (b) a groove entrance along a side surface of said first bone attachment component, and (c) a groove end wall opposite said groove entrance; and said corresponding engaging member has an engaging member length, $em_L$, along said base member upper surface, said engaging member length, $em_L$, along said base member upper surface being less than an overall length, $bm_L$, of said first base member.

9. The ankle replacement device of claim 8, wherein said upper surface structure comprises (1) at least two grooves separated from one another and extending in a front to rear direction along said upper surface, (2) a centrally-located track portion between said at least two grooves, and (3) outer track portions on opposite outer portions of said upper surface; and said lower surface depression of said first base member comprises (1) at least two rails separated from one another and extending in said front to rear direction along said lower surface depression so as to engagable with said at least two grooves, (2) a centrally-located depression portion between at least two rails so as to contact/engage with said centrally-located track portion, and (3) outer depression portions on opposite outer portions of said lower surface depression.

10. The ankle replacement device of claim 9, wherein said upper surface structure comprises two grooves separated from one another and extending in said front to rear direction along said upper surface; and said lower surface depression of said first base member comprises two rails separated from one another and extending in said front to rear direction along said lower surface depression.

11. The ankle replacement device of claim 10, wherein said second bone-engaging component further comprises a lower surface and a bone-connecting member along said lower surface, said bone-connecting member being operatively adapted to attach to a second bone.

12. The ankle replacement device of claim 11, wherein said bone-connecting member comprises two or more surface projections extending out from said lower surface, said two surface projections intersecting with one another along said lower surface.

13. The ankle replacement device of claim 6, wherein said upper surface structure has an arch of curvature having an arch angle ranging from about 135° to about 180° along any dissecting line thereof, and said lower surface depression has an arch of curvature having an arch angle ranging from about 30° to about 180° along any dissecting line thereof.

14. The ankle replacement device of claim 6, wherein each of said first bone-engaging component and said second bone-engaging component independently has an overall thickness of from about 0.5 centimeter (cm) to about 3.0 cm.

15. An ankle replacement device comprising:
(I) a first bone-engaging component operatively adapted to engage with a first bone, and comprising a first base member comprising a lower surface, said lower surface having an lower surface profile comprising (i) a lower surface portion surrounded by a lower surface periphery, and (ii) a lower surface depression surrounded by said lower surface portion, said lower surface depression having a dome-shaped configuration with a depression depth, $d_d$, and a depression surface area extending along said lower surface portion; and (II) a second bone-engaging component operatively adapted to engage with a second bone, and comprising an upper surface, said upper surface having an upper surface profile comprising (i) an upper surface portion surrounded by an outer periphery, and (ii) an upper surface structure surrounded by said outer periphery, said upper surface structure having a dome-shaped configuration with a structure height, $h_s$, extending above said outer periphery and a structure surface area extending along said upper surface portion;

said first bone-engaging component being engagable with said second bone-engaging component so that (i) at least a portion of said upper surface structure is positionable within said lower surface depression, and (ii) when said portion of said upper surface structure is positioned within said lower surface depression, said upper surface portion is movable relative to said lower surface portion;

wherein said upper surface structure comprises (1) at least two grooves separated from one another and extending in a front to rear direction along said upper surface, (2) a centrally-located track portion between said at least two grooves, and (3) outer track portions on opposite outer portions of said upper surface; and said lower surface depression of said first base member comprises (1) at least two rails separated from one another and extending in said front to rear direction along said lower surface depression so as to engagable with said at least two grooves, (2) a centrally-located depression portion between at least two rails so as to contact/engage with said centrally-located track portion, and (3) outer depression portions on opposite outer portions of said lower surface depression, and wherein said first base member further comprises a base member upper surface, a single base member bracket side wall extending upward from said base member upper surface, and a bone-connecting hole extending through said single base member bracket side wall.

16. The ankle replacement device of claim 15, wherein said first bone-engaging component further comprises a first bone attachment component sized and operatively adapted to be attached to the first bone, said first bone attachment component comprising a first component base, a first component base lower surface, a first component base upper surface, and at least one first component protruding member extending upward from said first component base upper surface.

17. The ankle replacement device of claim 16, wherein said first component base lower surface comprises an engaging groove therein, and said base member upper surface comprising a corresponding engaging member extending along said base member upper surface, said engaging groove and said corresponding engaging member being engagable with one another so as to engage said first bone attachment component with said first base member.

18. The ankle replacement device of claim 17, wherein (I) said engaging groove has (a)(i) a groove width, $g_{wls}$, along said first component base lower surface, and (ii) a groove width, $g_{wi}$, positioned between said first component base lower surface and said first component base upper surface, and said groove width, $g_{wls}$, along said first component base lower surface is less than said groove width, $g_{wi}$, positioned between said first component base lower surface and said first component base upper surface, (b) a groove length, $g_L$, along said first component base lower surface, said groove length, $g_L$, along said first component base lower surface being less than an overall length, $fc_L$, of said first bone attachment component, (c) a groove entrance along a side surface of said first bone attachment component, and (d) a groove end wall opposite said groove entrance; and (II) said corresponding engaging member has (1)(i) a engaging member width, $em_{wus}$, along said base member upper surface, and (ii) a engaging member width, $em_{wu}$, positioned away from said base member upper surface, and said engaging member width, $em_{wu}$, positioned away from said base member upper surface is greater than said engaging member width, $em_{wus}$, along said base member upper surface, and (2) an engaging member length, $em_L$, along said base member upper surface, said engaging member length, $em_L$, along said base member upper surface being less than an overall length, $bm_L$, of said first base member.

19. The ankle replacement device of claim 15, wherein each of said first bone-engaging component and said second bone-engaging component independently has an overall thickness of from about 0.5 centimeter (cm) to about 3.0 cm.

* * * * *